(12) United States Patent
Voorhees (10) Patent No.: US 8,092,990 B2
(45) Date of Patent: Jan. 10, 2012

(54) APPARATUS AND METHOD FOR DETECTING MICROSCOPIC ORGANISMS USING BACTERIOPHAGE

(75) Inventor: Kent J. Voorhees, Golden, CO (US)

(73) Assignee: Colorado School of Mines, Golden, CO (US)

(*) Notice: Subject to any disclaimer, the term of this patent is extended or adjusted under 35 U.S.C. 154(b) by 495 days.

(21) Appl. No.: 11/394,936

(22) Filed: Mar. 31, 2006

(65) Prior Publication Data

US 2007/0059725 A1    Mar. 15, 2007

Related U.S. Application Data

(60) Provisional application No. 60/667,291, filed on Mar. 31, 2005.

(51) Int. Cl.
*C12Q 1/70* (2006.01)

(52) U.S. Cl. .......................................................... 435/5

(58) Field of Classification Search .................... 435/5
See application file for complete search history.

(56) References Cited

U.S. PATENT DOCUMENTS

| | | |
|---|---|---|
| 3,839,175 A | 10/1974 | Keyes |
| 4,104,126 A | 8/1978 | Young |
| 4,764,473 A | 8/1988 | Matschke |
| 4,797,363 A | 1/1989 | Teodorescu et al. |
| 4,861,709 A | 8/1989 | Ulitzur et al. |
| 5,085,982 A | 2/1992 | Keith |
| 5,101,105 A | 3/1992 | Fenselau et al. |
| 5,126,024 A | 6/1992 | Bonelli et al. |
| 5,135,870 A | 8/1992 | Williams et al. |
| 5,168,037 A | 12/1992 | Entis et al. |
| 5,443,987 A | 8/1995 | Decicco et al. |
| 5,445,942 A | 8/1995 | Rabin et al. |
| 5,469,369 A | 11/1995 | Rose-Pehrsson et al. |
| 5,476,768 A | 12/1995 | Pearson et al. |
| 5,498,525 A | 3/1996 | Rees et al. |
| 5,498,528 A | 3/1996 | King |
| 5,550,062 A | 8/1996 | Wohltjen et al. |
| 5,620,845 A | 4/1997 | Gould et al. |
| 5,656,424 A | 8/1997 | Jurgensen et al. |
| 5,658,747 A | 8/1997 | Feldsine et al. |
| 5,679,510 A | 10/1997 | Ray et al. |
| 5,710,005 A | 1/1998 | Rittenburg |
| 5,723,330 A | 3/1998 | Rees et al. |
| 5,766,840 A | 6/1998 | Kim et al. |
| 5,789,174 A | 8/1998 | Mouton et al. |
| 5,824,468 A | 10/1998 | Scherer et al. |
| 5,859,375 A | 1/1999 | Danylewych-May et al. |
| 5,874,226 A | 2/1999 | Zeytinoglu et al. |
| 5,888,725 A | 3/1999 | Sanders |
| 5,914,240 A | 6/1999 | Sanders |
| 5,958,675 A | 9/1999 | Wicks et al. |
| 5,985,596 A | 11/1999 | Wilson |
| 6,004,770 A | 12/1999 | Nelson |
| 6,037,118 A | 3/2000 | Thomas et al. |
| 6,090,541 A | 7/2000 | Wicks et al. |
| 6,093,541 A | 7/2000 | Nelson |
| 6,177,266 B1 | 1/2001 | Krishnamurthy et al. |
| 6,183,950 B1 | 2/2001 | Vorhees et al. |
| 6,235,480 B1 | 5/2001 | Shultz et al. |
| 6,265,169 B1 | 7/2001 | Cortese et al. |
| 6,300,061 B1 | 10/2001 | Jacobs, Jr. et al. |
| 6,316,266 B1 | 11/2001 | Nelson |
| 6,322,783 B1 | 11/2001 | Takahashi |
| 6,355,445 B2 | 3/2002 | Cherwonogrodzky et al. |
| 6,428,976 B1 | 8/2002 | Chang et al. |
| 6,436,652 B1 | 8/2002 | Cherwonogrodzky et al. |
| 6,436,661 B1 | 8/2002 | Adams et al. |
| 6,461,833 B1 | 10/2002 | Wilson |
| 6,514,767 B1 | 2/2003 | Natan |
| 6,514,778 B2 | 2/2003 | Huang |
| 6,524,809 B1 | 2/2003 | Wilson |
| 6,544,729 B2 | 4/2003 | Sayler et al. |
| 6,555,312 B1 | 4/2003 | Nakayama |
| 6,580,068 B1 | 6/2003 | Tarver et al. |
| 6,660,437 B2 | 12/2003 | Friedrich et al. |
| 6,660,470 B1 | 12/2003 | Sanders |
| 6,787,360 B2 | 9/2004 | Agrawal et al. |
| 6,799,119 B1 | 9/2004 | Voorhees et al. |
| 6,824,975 B2 | 11/2004 | Hubscher et al. |
| 6,913,753 B2 | 7/2005 | Ramachandran |
| 7,034,113 B2 | 4/2006 | Olstein |
| 7,087,376 B2 | 8/2006 | Miller |
| 7,166,425 B2 | 1/2007 | Madonna et al. |
| 7,195,778 B2 | 3/2007 | Flashner-Barak et al. |
| 2002/0192676 A1 | 12/2002 | Madonna et al. |
| 2003/0175207 A1 | 9/2003 | Olstein et al. |
| 2004/0002126 A1* | 1/2004 | Houde et al. ................. 435/7.32 |
| 2004/0121403 A1 | 6/2004 | Miller |
| 2004/0137430 A1 | 7/2004 | Anderson et al. |
| 2005/0003346 A1 | 1/2005 | Voorhees et al. |
| 2005/0208475 A1 | 9/2005 | Best et al. |
| 2005/0250096 A1 | 11/2005 | Wheeler et al. |

(Continued)

FOREIGN PATENT DOCUMENTS

DE    43 14998    11/1994

(Continued)

OTHER PUBLICATIONS

Goodridge et al. "Development and characterization of a fluorescent-bacteriophage assay for detection of *Escherichia coli* O157:H7" Applied and Environmental Microbiology, 1999, 65(4):1397-1404.*

(Continued)

*Primary Examiner* — Amber D. Steele
*Assistant Examiner* — Bin Shen
(74) *Attorney, Agent, or Firm* — Dorsey & Whitney LLP (57) ABSTRACT

Methods and apparatus are provided for detection of microorganisms in a sample. Methods and apparatus of the invention are based on the specificity that phage, for example bacteriophage, have for target microorganisms, for example bacterium. Typically, phage adsorption to target microorganisms act as signal, or a signal target, for the presence of the target microorganism. Typically, the phage are labeled with a detectable signal. Apparatus of the invention are directed toward concentrating the phage adsorbed microorganisms at a predetermined site for flag dependent observation.

4 Claims, 4 Drawing Sheets

U.S. PATENT DOCUMENTS

| | | |
|---|---|---|
| 2005/0255043 A1 | 11/2005 | Hnatowich et al. |
| 2007/0059725 A1 | 3/2007 | Voorhees |
| 2007/0148638 A1 | 6/2007 | Madonna et al. |
| 2007/0178450 A1 | 8/2007 | Wheeler et al. |
| 2007/0249012 A1 | 10/2007 | Lye et al. |
| 2007/0275370 A1 | 11/2007 | Madonna et al. |
| 2009/0208996 A1 | 8/2009 | Kadurugamuwa et al. |
| 2009/0246752 A1 | 10/2009 | Voorhees et al. |
| 2009/0246753 A1 | 10/2009 | Voorhees |
| 2009/0258341 A1 | 10/2009 | Voorhees et al. |
| 2009/0286225 A1 | 11/2009 | Wheeler et al. |
| 2009/0286232 A1 | 11/2009 | Smith et al. |

FOREIGN PATENT DOCUMENTS

| | | |
|---|---|---|
| EP | 0168933 | 2/1986 |
| EP | 0228975 | 7/1987 |
| EP | 0439354 A2 | 7/1991 |
| EP | 1300082 A2 | 4/2003 |
| WO | WO 85/04189 | 9/1985 |
| WO | WO 88/04326 | 6/1988 |
| WO | WO 92/02633 | 9/1992 |
| WO | WO 93/11161 | 6/1993 |
| WO | WO 93/17129 A1 | 9/1993 |
| WO | WO 94/06931 | 3/1994 |
| WO | WO 94/13804 | 6/1994 |
| WO | WO 95/05483 A1 | 2/1995 |
| WO | WO 98/08944 | 3/1998 |
| WO | WO 98/18962 A1 | 5/1998 |
| WO | WO 00/10013 | 2/2000 |
| WO | WO 01/25395 | 4/2001 |
| WO | WO 02/061117 A1 | 8/2002 |
| WO | WO 03/035889 A2 | 5/2003 |
| WO | WO 03/087772 A2 | 10/2003 |
| WO | WO 03/087772 A3 | 10/2003 |
| WO | WO 2006/012371 | 2/2006 |
| WO | WO 2006/083292 | 8/2006 |
| WO | WO 2006/105504 | 10/2006 |
| WO | WO 2008/064241 | 5/2008 |

OTHER PUBLICATIONS

Goodridge et al. "Use of a fluorescent bacteriophage assay for detection of *Escherichia coli* O157:H7 in inoculated ground beef and raw milk", International Journal of Food Microbiology, 1999b, 47:43-50.*

U.S. Appl. No. 60/418,822, filed Oct. 15, 2002, Anderson et al.

International Search Report dated Apr. 25, 2007, in PCT/US2006/011958 filed Mar. 31, 2006 and published as WO 2006/105415 on Oct. 5, 2006.

Abbas-Hawks et al., "In Situ Methylation of Nucleic Acids Using Pyrolysis/Mass Spectrometry," Rapid Communications in Mass Spectrometry, vol. 10, pp. 1802-1806, 1996.

Barringer Research Limited, "Biological Agent Detection by Ion Mobility Spectrometery (Final Report)," CR96-012, pp. 1-25, Apr. 1996.

Basile et al., "Pathogenic Bacteria: Their Detection and Differentiation by Rapid Lipid Profiling with Pyrolysis Mass Spectrometry," Tends in Analytical Chemistry, vol. 00, No. 0, pp. 1-15, 1997, Elsevier Science B.V., The Netherlands.

Basile et al., "Direct Mass Spectrometric Analysis of in Situ Termally Hydrolyzed and Methylated Lipids from Whole Bacterial Cells," submitted to Analytical Chemistry, 34 pages, at least as early as Apr. 12, 2002.

Beverly et al., "A Rapid Approach for the Detection of Dipicolinic Acid in Bacterial Spores Using Pyrolysis/Mass Spectrometry," Rapid Communications in Mass Spectrometry, vol. 10, pp. 455-458, 1996.

Bordner et al., "Microbiological Methods for Monitoring the Environment—Water and Wastes," Dec. 1978, prepared in part under EPA Contract No. 68-03-0431, Environmental Monitoring and Support Laboratory, Office of Research and Development, USEPA, pp. i-xvi, 1-338, Cincinnati, Ohio.

Brockman et al., "Probe-Immobilized Affinity Chromatography/Mass Spectrometry", Analytical Chemistry, vol. 67, No. 24, pp. 4581-4585, Dec. 15, 1995, American Chemical Society, USA.

Bundy et al., "Lectin and Carbohydrate Affinity Caputre Surfaces for Mass Spectrometric Analysis of Microorganisms", Analytical Chemistry, vol. 73, No. 4, pp. 751-575, Feb. 15, 2001, American Chemical Society, USA.

Chatterjee et al. "A High Yielding Mutant of Mycobacteriophage L1 and Its Application as a Diagnostic Tool", FEMS Microbiology Letters, vol. 188, pp. 47-53, 2000.

Cluett et al., "The Envelope of Vaccinia Virus Reveals an Unusual Phospholipid in Golgi Complex Membranes," Journal of Cell Science, 109, pp. 2121-2131, 1996, Great Britain.

Crews et al., "Lipids Are Major Components of Human Immunodeficiency Virus: Modification of HIV Lipid Composistion, Membrane Organization, and Protein Conformation by AL-721," Drug Development Research 14:31-44, 1988.

Cudjoe et al., "Immunomagnetic Separation of *Salmonella* from Foods and Their Detection Using Immunomagnetic Particle (IMP)-ELISA," International Journal of Food Microbiology, Sep. 1995, pp. 11-25, vol. 27, No. 1, Elsevier Science, The Netherlands.

DeLuca et al., Pyrolysis-Mass Spectrometry Methodology Applied to Southeasst Asian Environmental Samples for Differentiating Digested and Undigested Pollens, Analytical Chemistry, vol. 58, 2439-2442, 1986.

DeLuca et al., "Direct Analysis of Bacterial Fatty Acids by Curie-Point Pyrolysis Tandem Mass Spectrometry," Analytical Chemical Society, vol. 62, No. 14, pp. 1465-1472, 1990.

DeLuca et al., "Direct Analysis of Bacterial Glycerides by Curie-Point Pyrolysis-Mass Spectrometry," Journal of Analytical and Applied Pyrolysis, vol. 23, pp. 1-14, 1992, Elsevier Science Publishers B.V., The Netherlands.

Dickinson et al., "New and Improved Strategies for the Rapid Detection and Differential Identification of Microbial Spores Using MALDI-TOFMS," Proceedings of the 50th ASMS Conference on Mass Spectrometry and Allied Topics, Orlando, Florida, 2 pages; Jun. 2-6, 2002.

Dubow, "Bacterial Identification—Use of Phages," section in Encyclopedia Virology, 2nd Edition, R.G. Webster and A. Granoff (eds.), pp. 137-139, 1999, Academic Press, San Diego, California.

Dziadkowiec et al., "The Detection of *Salmonella* in Skimmed Milk Powder Enrichments Using Conventional Methods and Immunomagnetic Separation," Letters in Applied Microbiology, 1995, pp. 361-364, vol. 20, The Society for Applied Bacteriology, Blackwell Science, UK.

Ember, "Chemical Warfare Agent Detectors Probe the Fogs of War," C&EN, pp. 26-32, Aug. 1, 1994.

Favrin et al., "Development and Optimization of a Novel Immunomagnetic Separation-Bacteriophage Assay for Detection of *Salmonella enterica* Serovar Enteritidis in Broth," Applied and Environmental Microbiology, Jan. 2001, pp. 217-224, vol. 67, No. 1, American Society for Microbiology, Washington, D.C.

Franz, et al., "Clinical Recognition and Management of Patients Exposed to Biological Warfare Agents," JAMA, vol. 278, No. 5, pp. 399-411, Aug. 6, 1997, USA.

Gantt et al., "Use of an Internal Control for Matrix-Assisted Laser Desorption/Ionization Time-of-Flight Mass Spectrometry Analysis of Bacteria", J Am Soc Mass Spectrom, 1999, pp. 1131-1137, vol. 10, American Society for Mass Spectrometry, Elsevier Science, The Netherlands.

Gharaibeh et al., : Characterization of Lipid Fatty Acids in Whole-Cell Microorganisms Using in Situ Supercritical Fluid Derivatization/Extraction and Gas Chromatography/Mass Spectrometry, Analytical Chemistry, vol. 68, pp. 2805-2810, 1996.

Girault et al., "Coupling of MALDI-TOF Mass Analysis to the Separation of Biotinylated Peptides by Magnetic Streptavidin Beads," Analytical Chemistry, vol. 68, No. 13, pp. 2122-2126, Jul. 1, 1996, American Chemical Society, USA.

Goodacre et al., "Rapid Identification Using Pyrolysis Mass Spectrometry and Artificial Neural Networks of *Propionibacterium acnes* Isolated from Dogs," Journal of Applied Bacteriology, vol. 76, pp. 124-134, 1994.

Grant et al., "Isolation of *Mycobacaterium paratuberculosis* from Milk by Immunomagnetic Separation," Applied and Environmental Microbiology, vol. 64, No. 9, pp. 3153-3158, Sep. 1998, American Society for Microbiology, USA.

Gross et al., "Mass Spectral Studies of Probe Pyrolysis Products of Intact Oligoribonucleotides," Nucleic Acids Research, vol. 5, No. 8, pp. 2695-2704, Aug. 1978, Department of Chemistry, University of Nebraska, Lincoln, Nebraska.

Hahner et al., "Matrix-Assisted Laser Desorption/Ionization Mass Spectrometry (MALDI) of Endonuclease Digests of RHA," Nucleic Acids Research, vol. 25, No. 10, pp. 1957-1964, 1997, Oxford University Press, UK.

Hendricker, "An Investigation into the Curie-point Pyrolysis-Mass Spectrometry of Glycyl Dipeptides," Journal of Analytical and Applied Pyrolysis, vol. 36, pp. 51-70, 1996.

Heylin, "The Chemicals of War," 1 page, C&EN, Mar. 9, 1998.

Higgins et al., "Competitive Oligonucleotide Single-Base Extension Combined with Mass Spectrometric Detection for Mutation Screening," BioTechniques, vol. 23, No. 4, pp. 710-714, Oct. 1997, Eaton Publishing Co., USA.

Hirsch, et al., "Rapid Detection of *Salmonella* spp. By Using Felix-O1 Bacteriophage and High-Performance Liquid Chromatography," Applied and Environmental Microbiology, vol. 45, No. 1, pp. 260-264, Jan. 1993, American Society for Microbiology, Washington, D.C.

Holland et al.,"Rapid Identification of Intact Whole Bacteria Based on Spectral Patterns Using Matrix-Assisted Laser Desorption/Ionization with Time-of-Flight Massd Spectrometry," Rapid Communications in Mass Spectrometry, vol. 10, pp. 1227-1232, 1996.

Holmes et al., "Coronaviridae: The Viruses and Their Replication," Fundamental Virology, Third Edition, B.N. Fields et al. (eds.), pp. 541-559, 1996, Lippincott-Raven Publishers, Philadelphia.

Huang et al., "Interplay Between Lipids and Viral Glycoproteins During Hemolysis and Fusion by Influenza Virus," The Journal of Biological Chemistry, vol. 261, No. 28, pp. 12911-12914, 1986.

Jenison et al., "Silicon-Based Biosensors for Rapid Detection of Protein or Nucleic Acid Targets," Clinical Chemistry, vol. 47, No. 10, pp. 1894-1900, Oct. 2001, American Association for Clinical Chemistry, Inc.

Jenison et al., "Thin Film Biosensor for Rapid Detection of mecA from Methicillin-resistant *Staphylococcus aureus*," Clinical Chemistry, vol. 46, No. 9, pp. 1501-1504, Sep. 2000, American Association for Clinical Chemistry, Inc.

Kermasha et al., "Comparative High-Performance Liquid Chromatographic Analyses of Cholesterol and Its Oxidation Products Using Diode-Array Ultraviolet and Laser Light-Scattering Detection," Journal of Chromatography A, vol. 685, pp. 229-235, 1994.

Kingsbury et al, "Rapid Detection and Identification of Infectious Agents," pp. i-xii, 1-296, Academic Press, Inc., Orlando, Florida 1985.

Kodikara et al., "Near On-Line Detection of Enteric Bacteria Using Lux Recombinant Bacteriophage," FEMS Microbiology Letter, vol. 83, pp. 261-265, 1991, Federation of European Microbiological Societies, Elsevier, The Netherlands.

Lamoureux et al., "Detection of *Campylobacter jejuni* in Food and Poultry Viscera Using Immunomagnetic Separation and Microtitre Hybridization", Journal of Applied Microbiology, vol. 83, pp. 641-651, 1997, The Society for Applied Bacateriology, UK.

Nyiendo, et al., "Preparation and Storage of High-Titer Lactic *Streptococcus* Bacteriophages," Applied Microbioilogy, vol. 27, No. 1, pp. 72-77, Jan. 1974, American Society for Microbiology.

Okrend et al., "Isolation of *Escherichia coli* O157:H7 Using O157 Specific Antibody Coated Magnetic Beads", Journal of Food Protection, Mar. 1992, pp. 214-217, 55, International Association of Milk, Food and Environmental Sanitarians.

Olsvik et al., "Magnetic Separation Techniques in Diagnostic Microbiology," Clinical Microbiology Reviews, vol. 7 No. 1, pp. 43-54, Jan. 1994.

Ostlund et al., "Quantification of Cholesterol Tracers by Gas Chromotography-Negative Ion Chemical Ionization Mass Spectrometry," Journal of Mass Spectrometry, 31:1291-1296, 1996.

Patzer et al., "Lipid Organization of the Membrane of Vesicular Stomatitis Virus," The Journal of Biological Chemistry, vol. 253, No. 13, pp. 4544-4550, Jul. 1978.

Pugh et al., "A Complete Protocol Using Conductance for Rapid Detection of *Salmonellas* in Confectionary Materials," Letters in Applied Microbiology, 1988, p. 23-27, vol. 7, The Society for Applied Microbiology, Blackwell Science, UK.

Pyle et al., "Sensitive Detection of *Escherichia coli* O157:H7 in Food and Water by Immunomagnetic Separation and Solid-Phase Laser Cytometry", Applied and Environmental Microbiology, May 1999, pp. 1966-1972, vol. 65, No. 5, American Society for Microbiology, Washington, D.C.

Rowe et al., "An Array Immunosensor for Simultaneous Detection of Clinical Analytes", Analytical Chemistry, Jan. 15, 1999, 71-#2, American Chemical Society, USA.

Ryzhov et al., "Characterization of the Protein Subset Desorbed by MALDI from Whole Bacterial Cells," Analytical Chemistry, Feb. 15, 2001, pp. 746-750, vol. 73, No. 4, American Chemical Society, Washington, D.C.

Sanderson, et al., "Surface Sampling Methods for *Bacillus anthracis* Spore Contamination," Emerging Infectious Diseases, vol. 8, No. 10, pp. 1145-1151, Oct. 2002.

Schlesinger, "Detecting Battlefield Toxins," Popular Science, 2 pages Oct. 1998.

Siuzdak, "Probing Viruses with Mass Spectrometry," *Journal of Mass Spectrometry*, vol. 33, pp. 203-211, 1998, John Wiley & Sons Ltd.

Skjerve et al., "Detection of *Listeria monocytogenes* in Foods by Immunomagnetic Separation," Applied and Environmental Microbiology, Nov. 1990, pp. 3478-3481, vol. 56, No. 11, American Society for Microbiology, Washington, DC.

Stankiewicz et al., "Assessment of Bog-body Tissue Preservation by Pyrolysis-Gas Chromatography/Mass Spectrometry," Rapid Communications in Mass Spectrometry, vol. 11, pp. 1884-1890, 1997.

Stewart et al., "The specific and sensitive detection of bacterial pathogens within 4 h using bacteriophage amplification," Journal of Applied Microbiology, vol. 84, pp. 777-783, 1998, The Society for Applied Microbiology, Blackwell Science, U.K.

Stewart, "In vivo bioluminescence: new potentials for microbiology," Letters in Applied Microbiology, vol. 10, pp. 1-8, 1990, The Society for Applied Microbiology, Blackwell Science, UK.

Strauss, et al., "Purification and Properties of Bacteriophage MS2 and of its Ribonucleic Acid," J. Mol. Biol., vol. 7, pp. 43-54, 1963, Elsevier Science, The Netherlands.

Sun et al., Use of Bioluminescent *Salmonella* for Assessing the Efficiency of Constructed Phage-Based Biosorbent, *Journal of Industrial Microbiology & Biotechnology*, 2000, vol. 25, pp. 273-275, Nature Publishing Group.

Sun et al., "Use of Bioluminescent *Salmonella* for Assessing the Efficiency of Constructed Phage-Based Biosorbent," Journal of Industrial Microbiology & Biotechnology, vol. 27, No. 2, pp. 126-128, Aug. 2001.

Tan et al., "Rapid Simultaneous Detection of Two Orchid Viruses Using LC- and/or MALDI-mass Spectrometry," *Journal of Virological Methods*, vol. 85, pp. 93-99, 2000, Elsevier Science B.V., The Netherlands.

Tas et al., "Characterization of Virus Infected Cell Cultures by Pyrolysis/Direct Chemical Ionization Mass Spectrometry," Biomedical and Environmental Mass Spectrometry, vol. 18, pp. 757-760, 1989.

Thomas et al., "Viral Characterization by Direct Analysis of Capsid Proteins," Analytical Chemistry, vol. 70, No. 18, pp. 3863-3867, Sep. 15, 1998.

Tremblay, "DARPA Expands R&D on Biowarfare Defense Tools," 1 page, C&EN, Feb. 16, 1998.

Van Der Wolf et al., "Immunomagnetic separation of *Erwinia caratovora* subsp. Astroseptica from potato peel extracts to improve detection sensitivity on a crystal violet pectate medium or by PCR," Journal of Applied Bacteriology, vol. 80, pp. 487-495, May 1996, Blackwell Science, UK.

Van Hoeven et al., "Studies on Plasma Membranes," Biochimica et Biophysica Acta, vol. 380, pp. 1-11, 1975, Elesevier Scientific Publication Company, The Netherlands.

Voorhees et al., "An Investigation of the Pyrolysis of Oligopeptides by Curie-point Pyrolysis-tandem Mass Spectrometry," Journal of Analytical and Applied Pyrolysis, vol. 30, pp. 1-16, 1994, Elsevier Science B.V., The Netherlands.

Wang et al., "Investigation of Spectral Reproducibility in Direct Analysis of Bacteria Proteins by Matrix-Assisted Laser Desorption/Ionization Time-of-Fight Mass Spectrometry," Rapid Communications in Mass Spectrometry, vol. 12, pp. 456-464, 1998, John Wiley & Sons, Ltd., Hoboken, USA.

Windig et al., "Control of the Absence of Deae-Polysaccharides in Deae-Sephadex Purified Poliovirus Suspensions by Pryolysis Mass Spectrometry," Develop. Biol Standard, vol. 47, pp. 169-177, 1981.

Wyatt et al., "Immunoassays for Food-poisoning Bacteria and Bacterial Toxins," Nov. 1992, pp. i-xiii, 1-129, James & James (Science Publishers) Ltd. and Chapman & Hall, London, Great Britain.

Yates et al., "Method to Compare Collison-Induced Dissociation Spectra of Peptides: Potential for Library Searching and Subtractive Analysis," Analytical Chemisry, vol. 70, pp. 3557-3565, 1998.

Yu et al, "Immunomagnetic-Electrochemiluminescent Detection of *Escherichia coli* O157 and *Salmonella typhimurium* in Foods and Environmental Water Samples," Applied and Environmental Microbiology, vol. 62, No. 2, pp. 587-592, Feb. 1996, American Society for Microbiology, Washington, D.C.

Bird et al., "Single-Chain Antigen-Binding Proteins," *Science*, 1988, vol. 242, pp. 423-426.

Carter, "Potent antibody therapeutics by design," *Nature Reviews Immunology*, 2006, vol. 6, pp. 343-357.

Casini et al., "In vitro papillomavirus capsid assembly analyzed by light scattering," *Virology*, 2004, vol. 325, pp. 320-327.

Garcia, et al., "The Genome Sequence of *Yersinia pestis* Bacteriophage φA1122 Reveals an Intimate History with the Coliphage T3 and T7 Genomes," *Journal of Bacteriology*, Sep. 2003, vol. 185, No. 17, pp. 5248-5262.

Haynes et al., "Surface Enhanced Raman Spectroscopy," *Anal. Chem.*, 2005, pp. 339A-346A.

Holliger et al., "Diabodies: Small bivalent and bispecific antibody fragments," *Proc. Natl. Acad. Sci. U.S.A.*, 1993, vol. 90, pp. 6444-6448.

Holliger et al., "Engineered antibody fragments and the rise of single domains," *Nature Biotechnology*, 2005, vol. 23, No. 9, pp. 1126-1136.

Huston et al., "Protein engineering of antibody binding sites: Recovery of specific activity in an anti-digoxin single-chain Fv analogue produced in *Escherichia coli,*" *Proc. Natl. Acad. Sci.* U.S.A., 1988, vol. 85, pp. 5879-5883.

Lech, et al., "Section III Vectors Derived from Lambda and Related Bacteriophages," Current Protocols in Molecular Biology, Frederick M. Ausubel, et al. (Editor), ISBN: 978-0-471-50338-5, 1987, 34 pages.

Madonna, et al., "On-probe sample pretreatment for the detection of proteins above 15 Kda from whole cell bacteria by matrix-assisted laser desorption/ionization time-of-flight mass spectrometry," *Rapid Communications in Mass Spectrometry*, 2000, vol. 14, p. 2220-2229.

Sambrook et al., Molecular Cloning: A Laboratory Manual, Second Edition, 1889, Cold Spring Harbor Laboratory Press, 27 pages (Title page and Table of Contents).

Tomlinson et al., "Methods for Generating Multivalent and Bispecific Antibody Fragments," *Methods Enzymol.*, 2000, vol. 326, pp. 461-479.

Ward et al., "Binding activities of a repertoire of single immunoglobulin variable domains secreted from *Escherichia coli,*" *Nature*, 1989, vol. 341, pp. 544-546.

Abdel-Hamid et al., "Flow-through immunofiltration assay system for rapid detection of *E. coli* O157:h7," *Biosens. Bioelectron.*, 1999, vol. 14, No. 3, pp. 309-316.

Cardullo, "Nonradioactive Fluorescence Resonance Energy Transfer," *Nonradioactive Labeling and Detection of Biomolecules*, C. Kessler, Editor, Springer-Verlag, New York, 1992, pp. 414-423.

Dabrowska et al., "The effect of bacteriophages T4 and HAP1 on in vitro melanoma migration," *BMC Microbiol.*, 2009, vol. 9, pp. 9-13.

Dictionary.com, "Microorganism," 2009, updated, //dictionary.reference.com/browse/microorganism, pp. 1-3.

Fines et al., "Activity of linezolid against Gram-positive cocci possessing genes conferrring resistance to protein synthesis inhibitors," *J. Antimicrob. Chemoth.*, 2000, vol. 45, pp. 797-802.

Heid, et al., "Real time quantitative PCR," *Genome Research*, Oct. 1996, vol. 6, No. 10, pp. 986-994.

Krishnamurthy et al., "Rapid Identification of Bacteria by Direct Matrix-assisted Laser Desorption/Ionization Mass Spectrometric Analysis of Whole Cells," *Rapid Communications in Mass Spectrometry*, 1966, vol. 10, pp. 1992-1996.

Mandeville et al., "Diagnostic and Therapeutic Applications of Lytic Phages," *Anal. Lett.*, 2003, vol. 36, No. 15, pp. 3241-3259.

Van De Plas et al., "Colloidal Gold as a Marker in Molecular Biology: The Use of Ultra-Small Gold Particles," *Nonradioactive Labeling and Detection of Biomolecules*, C. Kessler, Editor, Spring-Verlag, New York, 1992, pp. 116-126.

Wu et al., "A hairpin aptamer-based electrochemical biosensing platform for the sensitive detection of proteins," *Biomaterials*, 2009, vol. 30, pp. 2950-2955.

Cairns et al., "Quantitive Models of in Vitro Bacteriophage—Host Dynamics and Their Application to Phage Therapy," *PLos Pathogens*, 2009, vol. 5, No. 1, pp. 1-10.

Le Cacheux et al., "Quantitative Analysis of Cholesterol and Cholesterol Ester Mixtures Using Near-Infared Fourier Transform Raman Spectroscopy," Applied Spectroscopy, vol. 50, No. 10, pp. 1253-1257, 1996.

Lynn et al., "Identification of Enterobacteriaceae Bacteria by Direct Matrix-assisted Laser Desorption/Ionization Mass Spectrometric Analysis of Whole Cells," vol. 13, No. 20, pp. 2022-2027, 1999, John Wiley & Sons, Ltd., Hoboken USA.

Madonna et al., "Detection of Bacteria from Biological Mixtures Using Immunomagnetic Separation Combined with Matrix-Assisted Laser Desorption/Ionization Time-of-Flight Mass Spectrometry," Rapid Communications in Mass Spectrometry, vol. 15, No. 13, pp. 1068-1074, Jun. 6, 2001, John Wiley & Sons, Ltd., Hoboken, USA.

Madonna et al., "Detection of *Escherichia coli* Using Immunomagnetic Separation and Bacteriophage Amplification Coupled with Matrix-assisted laser Desorption/Ionization Time-of-flight Mass Spectrometry," Rapid communications in Mass Spectrometry, published online Dec. 24, 2002 in Wiley InterScience (www.interscience.wiley.com), pp. 257-263, vol. 17, John Wiley & Sons, Ltd.

Madonna et al., "Isolation and Enrichment of *Salmonella* on Immunomagnetic Beads Prior to Detection by MALDI-TOFMS" (extended abstract), *49th ASMS Conference on Mass Spectrometry and Allied Topics*, May 27-31, 2001, Session Code: MPI, Slot: 204, 1 page, USA.

Madonna et al., "Investigation of Cell Culture Media Infected with Viruses by Pyrolysis Mass Spectrometry: Implications for Bioaerosol Detection," American Society for Mass Spectrometry, vol. 10, No. 6, pp. 502-511 Jun. 1999.

Madonna, et al., "Investigation of Viruses Using Pyrolysis Mass Spectrometry," [appears to be an internal power point presentation], 14 pages, 1999, 10(6):502-511.J. Am.

Mansfield et al., "Immunomagnetic Separation as an Alternative to Enrichmnet Broths for *Salmonella* Detection", Letters in Applied Microbiology, vol. 16, pp. 122-125, 1993.

Marple et al., "Aerosol Sample Acquisition for Chemical and Biological Agent Detection," Abstract, Report No. ARO-25616.1-CHS, Army Research Office, Dec. 1, 1989.

Meuzelaar et al., "Characterization of Leukemic and Normal White Blood Cells by Curie-Point Pyrolysis-Mass Spectrometry. Biochemical Interpretation of Some of the Differences in the Pyrolysis Patterns," Journal of Analytical and Applied Pyrolysis, vol. 3, pp. 111-129, 1981.

Munoz-Barroso et al., "Dynamic Properties of Newcastle Disease Virus Envelope and Their Relations with Viral Hemagglutinin-Neuraminidase Membrane Glycoprotein," Biochimica et Biophysica Acta, vol. 1327, pp. 17-31, 1997.

Nakamura et al., "A Visualizatoin Method of Filamentous Phage Infection and Phage-Derived Proteins in *Escherichia coli* Using Biotinylated Phages," Biophysical and Biophysical Research Communications, vol. 289, No. 1, pp. 252-256 Nov. 2001.

Nelson et al., "Mass Spectrometric Immunoassay", Analytical Chemistry, vol. 67, No. 7, pp. 1153-1158, Apr. 1, 1995, American Chemical Society, USA.

Krueger et al., "The Kinetics of the Bacterium-Bacteriophage Reaction," The Journal of General Physiology, 1930, vol. 14, pp. 223-254.

In the US Patent and Trademark Office, U.S. Appl. No. 10/249,452, Non-Final Office Action dated Feb. 23, 2005, 12 pages; and corresponding response dated Aug. 26, 2005, 17 pages.

In the US Patent and Trademark Office, U.S. Appl. No. 10/249,452, Non-Final Office Action dated Feb. 7, 2006, 9 pages; and corresponding response dated Aug. 7, 2006, 7 pages, and supplemental response dated Aug. 30, 2006, 6 pages.

In the US Patent and Trademark Office, U.S. Appl. No. 10/823,294, Final Office Action dated Dec. 3, 2007, 14 pages; and corresponding response and RCE dated Mar. 3, 2008, 14 pages.

In the US Patent and Trademark Office, U.S. Appl. No. 10/893,294, Non-Final Office Action dated Apr. 25, 2008, 11 pages; and corresponding response dated Aug. 25, 2008, 5 pages.

In the US Patent and Trademark Office, U.S. Appl. No. 10/823,294, Non-Final office Action dated Jul. 23, 2007, 20 pages; and corresponding response dated Nov. 21, 2007, 24 pages.

In the US Patent and Trademark Office, U.S. Appl. No. 10/823,294, Non-Final Office Action dated Sep. 30, 2008, 8 pages; no response made.

* cited by examiner

FIG. 4

APPARATUS AND METHOD FOR DETECTING MICROSCOPIC ORGANISMS USING BACTERIOPHAGE

CROSS-REFERENCE TO RELATED APPLICATIONS

This application claims priority to and incorporates by reference U.S. provisional patent application Ser. No. 60/667,291, filed Mar. 31, 2005.

STATEMENT REGARDING FEDERALLY SPONSORED RESEARCH

The invention was made with United States Government support under Project No. 4-42209 awarded by the Armed Forces Institute for Pathology. The United States Government has certain rights in the invention.

The application is related to U.S. patent application Ser. No. 10/823,294, filed Apr. 12, 2004 and U.S. patent application Ser. No. 10/249,452, filed Apr. 10, 2003, each of which is incorporated by reference in its entirety.

BACKGROUND OF THE INVENTION a. Field of the Invention

The invention relates generally to the field of microscopic organism detection, and more particularly to the detection of microscopic organisms utilizing bacteriophage or other like viral organisms.

b. Statement of the Problem

Standard microbiological methods for detection of microorganisms have relied on substrate-based assays to test for the presence of specific bacterial pathogens. See Robert H. Bordner, John A. Winter, and Pasquale Scarpino, Microbiological Methods For Monitoring The Environment, EPA Report No. EPA-600/8-78-017, U.S. Environmental Protection Agency, Cincinnati, Ohio, 45268, December 1978. These techniques are generally easy to perform, do not require expensive supplies or laboratory facilities, and offer high levels of selectivity. However, substrate-based assay methods are slow, requiring the growth and cultivation of pure cultures of the targeted organism on appropriate substrate. The growth period can take as long as twenty-four hours and in some cases longer. This time constraint severely limits the effectiveness of substrate-based assays to provide rapid response to the presence of virulent strains of microorganisms.

Molecular biology based techniques are quickly gaining acceptance as valuable alternatives to standard microbiological tests like the substrate-based assay. Serological methods have been widely employed to evaluate a host of matrices for targeted microorganisms. See David T. Kingsbury and Stanley Falkow, Rapid Detection And Identification of Infectious Agents, Academic Press, Inc., New York, 1985 and G. M. Wyatt, H. A. Lee, and M. R. A. Morgan, Chapman & Hall, New York, 1992. These tests focus on using antibodies to first trap and then separate targeted organisms from other constituents in complicated biological mixtures. Once isolated, the captured organism can be concentrated and detected by a variety of different techniques that do not require cultivating the biological analyte. One such approach, termed "immunomagnetic separation" (IMS), involves immobilizing antibodies to spherical, micro-sized magnetic or paramagnetic beads and using these beads to trap targeted microorganisms from liquid media. The beads are easily manipulated under the influence of a magnetic field facilitating the retrieval and concentration of targeted organisms. Moreover, the small size and shape of the beads allow them to become evenly dispersed in the sample, accelerating the rate of interaction between bead and target. These favorable characteristics lead to reductions in assay time and help streamline the analytical procedure, making it more applicable for higher sample throughput and automation.

Downstream detection methods previously used with IMS include ELISA (Kofitsyo S. Cudjoe, Therese Hagtvedt, and Richard Dainty, "Immunomagnetic Separation of Salmonella From Foods And Their Detection Using Immunomagnetic Particle", International Journal of Food Microbiology, 27 (1995), pp. 11-25), dot blot assay (Eystein Skjerve, Liv Marit Rorvik, and Orjan Olsvick, "Detection Of Listeria Monocytogenes In Foods By Immunomagnetic Separation", Applied and Environmental Microbiology, November 1990, pp. 3478-3481), electrochemiluminescence (Hao Yu and John G. Bruno, Immunomagnetic-Electrochemiluminescent Detection Of *Escherichia coli* O157 and *Salmonella typhimurium* In Foods and Environmental Water Samples", Applied and Environmental Microbiology, February 1996, pp. 587-592), and flow cytometry (Barry H. Pyle, Susan C. Broadway, and Gordon A. McFeters, "Sensitive Detection of *Escherichia coli* O157:H7 In Food and Water By Immunomagnetic Separation And Solid-Phase Laser Cytometry", Applied and Environmental Microbiology, May 1999, pp. 1966-1972). Although these tests provide satisfactory results, they are laborious to perform and give binary responses (yes/no) that are highly susceptible to false-positive results due to cross-reactivity with non-target analytes. Another method for identifying whole cellular microorganisms uses IMS coupled to matrix-assisted laser desorption/ionization (MALDI) time-of-flight (TOF) mass spectrometry (MS) (Holland et al., 1996; van Barr, 2000; Madonna et al., 2000).

These alternative approaches can offer faster results than do traditional microbiology based methods. However, they do not achieve the sensitivity levels that substrate-based assays do, are more expensive, and typically require more highly trained technicians than do classical substrate-based methods.

Other molecular biology techniques have received a great deal of recent attention toward microorganism detection, including Polymerase Chain Reaction (PCR). PCR detection of specific microorganisms in a sample involves extraction of the genetic material (RNA and/or DNA) in a sample, amplification of a target genetic sequence specific to the microorganism of interest, and then detection of the amplified genetic material. PCR techniques offer high selectivity owing to the uniqueness of the detected genetic material, high sensitivity because of the substantial amplification of the target genetic material, and rapid results owing to the potentially fast amplification process. However, PCR instruments and reagents are quite expensive and highly trained technicians are needed to perform the tests.

Some attempts have been made to improve upon substrate-based classical bacterial detection methods using bacteriophage infection and amplification. Bacteriophages are viruses that have evolved in nature to use bacteria as a means of replicating themselves. A bacteriophage (or phage) does this by attaching itself to a bacterium and injecting its genetic material into that bacterium, inducing it to replicate the phage from tens to thousands of times. Some bacteriophage, called lytic bacteriophage, rupture the host bacterium releasing the progeny phage into the environment to seek out other bacteria to infect. The total incubation time for phage infection of a bacterium, phage multiplication (amplification) in the bacterium, and release of the progeny phage after lysis can take as little as an hour depending on the phage, the bacterium, and the environmental conditions. Microbiologists have isolated and characterized over 5,000 phage species, including many that specifically target bacteria at the species or even the strain level. U.S. Pat. No. 5,985,596 issued Nov. 16, 1999 to Stuart Mark Wilson and U.S. Pat. No. 6,461,833 B1 issued Oct. 8, 2002 to Stuart Mark Wilson describe such a phage-based assay method. It comprises a lytic phage infection of a sample that may contain bacteria of interest. This is followed by removal of free phage from the sample, target bacteria lysis, and then infection of a second bacterium by the progeny phage where the second bacterium has a shorter doubling time than does the target bacterium. The prepared sample is grown on a substrate and the formation of plaques indicates the presence of the target bacterium in the original sample. This method can shorten the assay time of a traditional substrate-based assay, though assays still take many hours or days because of the requisite culture incubation times. Another problem with the method is that it can only be applied to detect bacterium for which a non-specific phage exists that also infects a more rapidly doubling bacterium than the target bacterium. Usage of a nonspecific phage opens the possibility of cross-reactivity to at least the second bacterium in test samples. Thus, this phage-based, plaque assay method is not rapid, can only be applied if a suitable non-specific phage is available, is prone to cross-reactivity problems, and must be performed in a lab setting.

Other bacterial pathogen detection methods utilize bacteriophage that have been genetically modified with detectable marker or reporter marker genes which is only expressed if a target bacterium is present in a sample and is then infected by the modified phage. U.S. Pat. No. 4,861,709 issued Aug. 29, 1989 to Ulitzur et al. is a typical example. A phage that specifically infects a target pathogen is modified to include a lux gene. When the modified phage is added to a sample containing the target bacterium, the phage infects the bacterium, luciferase is produced in the bacterium, and light is emitted. U.S. Pat. No. 5,824,468 issued Oct. 20, 1998 to Scherer et al. describes a similar method. In addition to luciferase-producing gene markers, Scherer et al. describes gene markers that are expressed as detectable proteins or nucleic acids. U.S. Pat. No. 5,656,424 issued Aug. 12, 1997 to Jurgensen et al. describes a method utilizing luciferase (or β-galactosidase) reporter phage to detect mycobacteria. It further describes testing for antibiotic susceptibility. U.S. Pat. No. 6,300,061 B1 issued Oct. 9, 2001 to Jacobs, Jr. et al. describes yet another method for detecting mycobacteria using genetically modified phage, which produces one of several reporter molecules after bacterial infection, including luciferase. U.S. Pat. No. 6,555,312 B1 issued Apr. 29, 2003 to Hiroshi Nakayama describes a method utilizing a gene that produces a fluorescent protein marker rather than a luminescent one. All of these methods take implicit advantage of phage amplification within infected bacteria. For each target bacterium infected in a sample, the marker gene is expressed many times over as the progeny phage are produced. U.S. Pat. No. 6,544,729 B2 issued Apr. 8, 2003 to Sayler et al. adds an additional amplification process. A phage's DNA is modified to include a lux gene. A bioreporter cell is also modified to include a lux gene. The genetically modified phage and bioreporter cells are added to a sample. If the phage infects target bacteria, the target bacteria are induced to produce not only luciferase but also acyl en homoserine lactone N-(3-oxohexanoyl) homoserine lactone (AHL). AHL finds its way into the bioreporter cells, stimulating the production of additional light and additional AHL, which in turn finds its way into additional bioreporter cells resulting in the production of even more light. Thus, an amplified light signal is triggered by the phage infection of the target bacteria. In principle, all of these methods utilizing genetically modified phage make possible: 1) high selectivity because they utilize selectively infecting phage; 2) high sensitivity because the marker gene products can be detected at low levels; and 3) results that are faster than substrate-based methods because the signal can be detected within one or two phage infection cycles. They have two potential drawbacks: first, they are expensive and can be difficult to implement because suitable phage must be genetically modified for each pathogen to be tested; and second, they often require an instrument to detect the marker signal (light), driving up the cost of tests utilizing genetically modified phage.

U.S. Pat. No. 5,888,725 issued Mar. 30, 1999 to Michael F. Sanders describes a method utilizing unmodified, highly specific lytic phages to infect target bacteria in a sample. Phage-induced lysis releases certain nucleotides from the bacterial cell such as ATP that can be detected using known techniques. Detecting increased nucleotide concentrations in a sample after phage infection indicates the presence of target bacteria in the sample. U.S. Pat. No. 6,436,661 B1 issued Aug. 20, 2002 to Adams et al. describes a method whereby a phage is used to infect and lyse a target bacterium in a sample releasing intracellular enzymes, which react in turn with an immobilized enzyme substrate, thereby producing a detectable signal. While these methods have the advantage of using unmodified phage, they do not derive any benefit from phage amplification. The concentration of detected markers (nucleotides or enzymes) is directly proportional.

U.S. Pat. No. 5,498,525 issued Mar. 12, 1996 to Rees et al. describes a pathogen detection method using unmodified phage and phage amplification to boost the detectable signal. The method calls for adding a high concentration of a lytic phage to a sample. The sample is incubated long enough to allow the phage to infect the target bacteria in the sample. Before lysis occurs, the sample is treated to remove, destroy, or otherwise inactivate the free phage in the sample without affecting the progeny phage being replicated within infected bacteria. If necessary, the sample is subsequently treated to neutralize the effects of any anti-viral agent previously added to the sample. The progeny phage released by lysis are detected using a direct assay of the progeny phage or by using a genetically modified bioreporter bacterium to generate a signal indicating the presence of progeny phage in the sample. In either case, the measured signal is proportional to the number of progeny phage rather than the number of target bacteria in the original sample and, thus, is enhanced as a result of phage amplification. One disadvantage of this method is that it requires free phage in the treated sample to be destroyed, removed, or inactivated followed by reversal of the virucidal conditions such that progeny phage will remain viable after lysis. These additional processes complicate assays utilizing the method and make them more expensive.

What is needed in the art is a detection method combining the sensitivity, simplicity, and/or low cost of substrate-based assays with the rapid results offered by molecular biology diagnostic tests.

Against this backdrop the present invention has been developed.

BRIEF SUMMARY OF THE INVENTION

The invention solves the above problems, as well as other problems of the prior art, by providing methods and apparatus for fast and effective detection of microorganisms using the principle of microphage (hereinafter referred to as "phage") adsorption to the surface of target microorganisms, the phage adsorption acting as a signal or signal target for the presence of a specific microorganism. Specificity of the methods and assays of the invention are based on the specificity of the particular phage for a particular type, species or strain of microorganism.

The invention provides methods and apparatus for detecting microorganisms through specific interactions of the phage with the outside surface of a target microorganism, where the phage acts as a signal, or a signal target, for the presence of the target microorganism. In some embodiments the phage is highly specific for the target microorganism, i.e., shows high levels of specificity for a particular microorganism. In other embodiments the phage has broader specificity for numerous different types of microorganisms, i.e., shows variable specificity for a target microorganism and is able to interact with numerous different types of target microorganism.

In one preferred embodiment, phage is conjugated with a suitable flag, for example a colloidal gold nanoparticle, to act as a signal for the presence of target microorganisms. Flagged phage interact with the surface of target microorganism, are then bound or adsorbed to microorganism, to form a flagged phage-microorganism complex. The flagged phage-microorganism complex can then be captured and concentrated for detection. In some embodiments detection is through visual inspection of the concentrated flagged phage-microorganisms, e.g., concentrated phage labeled with colloidal gold nanoparticles can appear as a gold line or shape dependent on the phage concentration parameters. Typically, hundreds to thousands of flagged phage interact and become adsorbed to each target microorganism providing an enhanced detection signal.

In one example, a flagged phage that is specific to a target microorganism is introduced into a sample to be tested. The amount of flagged phage is preferably the amount required for statistically relevant detection of the flag signal. If the microorganism is present, the flagged phage specifically binds to the surface of the microorganism, thereby labeling the microorganism as present in the sample. Labeled microorganisms are captured and concentrated for convenient detection using immunoabsorption or other like technologies, i.e., as appropriate for the particular flag. If the target microorganism in not present, the flagged phage does not provide a detectable or statistically significant signal. The flagged phage-microorganism complex can be detected in any suitable fashion for the particular flag, for example, colloidal gold nanoparticles can be detected using an immobilization zone, where the gold nanoparticles are concentrated within a device, for example on a lateral flow strip or ELISA based assay. The concentrated flagged microorganisms (gold nanoparticles) are thereby visible with the eye, e.g., as a gold line across the lateral flow strip device or as a gold circle in an ELISA based device.

In one aspect, the invention provides a highly specific microorganism detection method.

In another aspect, the invention provides a broad-spectrum microorganism detection method.

In still another aspect, the invention provides a microorganism detection method that gives rapid results as compared to most existing microorganism detection methods.

In still another aspect, the invention provides a microorganism detection method that is inexpensive relative to existing microorganism detection methods.

In still another aspect, the invention provides a microorganism detection method that is simple to perform and does not require highly skilled technicians or complex instrumentation.

In still another aspect, the invention provides a microorganism detection method that can be performed in the field or at a point of care, for example, to test a sample found in the room of a building.

In still another aspect, the invention provides a microorganism detection method that uses the detection of a specific phage biomarker as a surrogate for detecting target microorganism present in a sample.

In still another aspect, the invention provides a microorganism detection method that utilizes highly specific phage interactions with target microorganism surfaces as a means of specifically detecting the presence of a target microorganism in a sample.

It still another aspect, the invention provides a microorganism detection method that can be used to detect any microorganism for which a suitable phage exists.

In still another aspect, the invention provides a microorganism detection method that utilizes lateral flow strips to detect phage and thereby detect the presence of target microorganism in a sample.

The above summary is intended to illustrate some examples of the aspects, features, and advantages of the invention so that the invention can be better understood. In some embodiments of the invention, only one of the above aspects may be realized, and in others a plurality of such aspects of the invention may be realized. However, the above aspects of the invention are intended to be exemplary, not all inclusive, so there will be instances in which none of the above aspects are realized in a particular embodiment.

Numerous other features, objects, and advantages of the invention will become apparent from the following description when read in conjunction with the accompanying drawings.

DETAILED DESCRIPTION OF THE INVENTION

The methods and apparatus of the invention rely on the usage of phage, e.g., bacteriophage, to detect the presence of target microscopic organisms (microorganisms), such as a bacterium, in a sample.

The invention provides methods and apparatus for detecting microorganisms through specific interactions of the phage with the outside surface of the target microorganism. When the phage adsorbs to the surface of the microorganism the phage acts as a signal, or a signal target, for the presence of the target microorganism. Embodiments of the invention further provide convenient and inexpensive methods and apparatus for concentrating and detecting the phage bound microorganism complexes.

The disclosed invention offers a combination of specificity, sensitivity, simplicity, speed, and/or cost which is superior to any currently known microorganism detection method. The method taught herein relies on the usage of phage to indirectly detect the presence of one or more target microorganisms in a sample.

Bacteriophage (Phage):

In this disclosure, the terms "bacteriophage" and "phage" include bacteriophage, phage, mycobacteriophage (such as for TB and paraTB), mycophage (such as for fungi), mycoplasma phage or mycoplasmal phage, and any other term that refers to a virus that can invade living bacteria, fungi, mycoplasmas, protozoa, and other microscopic living organisms and uses them to replicate itself. Here, "microscopic" means that the largest dimension is one millimeter or less. Note that for purposes of the present invention any phage that can specifically adsorb with a microorganism can be useful in the present invention, however, for simplicity sake, the invention is often described in relation to bacteriophage and bacterium.

Bacteriophage are viruses that have evolved in nature to use bacteria as a means of replicating themselves. A bacteriophage does this by attaching itself to a bacterium and injecting its DNA into that bacterium, inducing it to replicate the bacteriophage hundreds or even thousands of times. Some bacteriophage, called lytic bacteriophage, rupture the host bacterium, releasing the progeny phage into the environment to seek out other bacteria. The total incubation time for phage infection of a bacterium, phage multiplication or amplification in the bacterium, to lysing of the bacterium takes anywhere from tens of minutes to hours, depending on the bacteriophage and bacterium in question and the environmental conditions.

Figure 1:
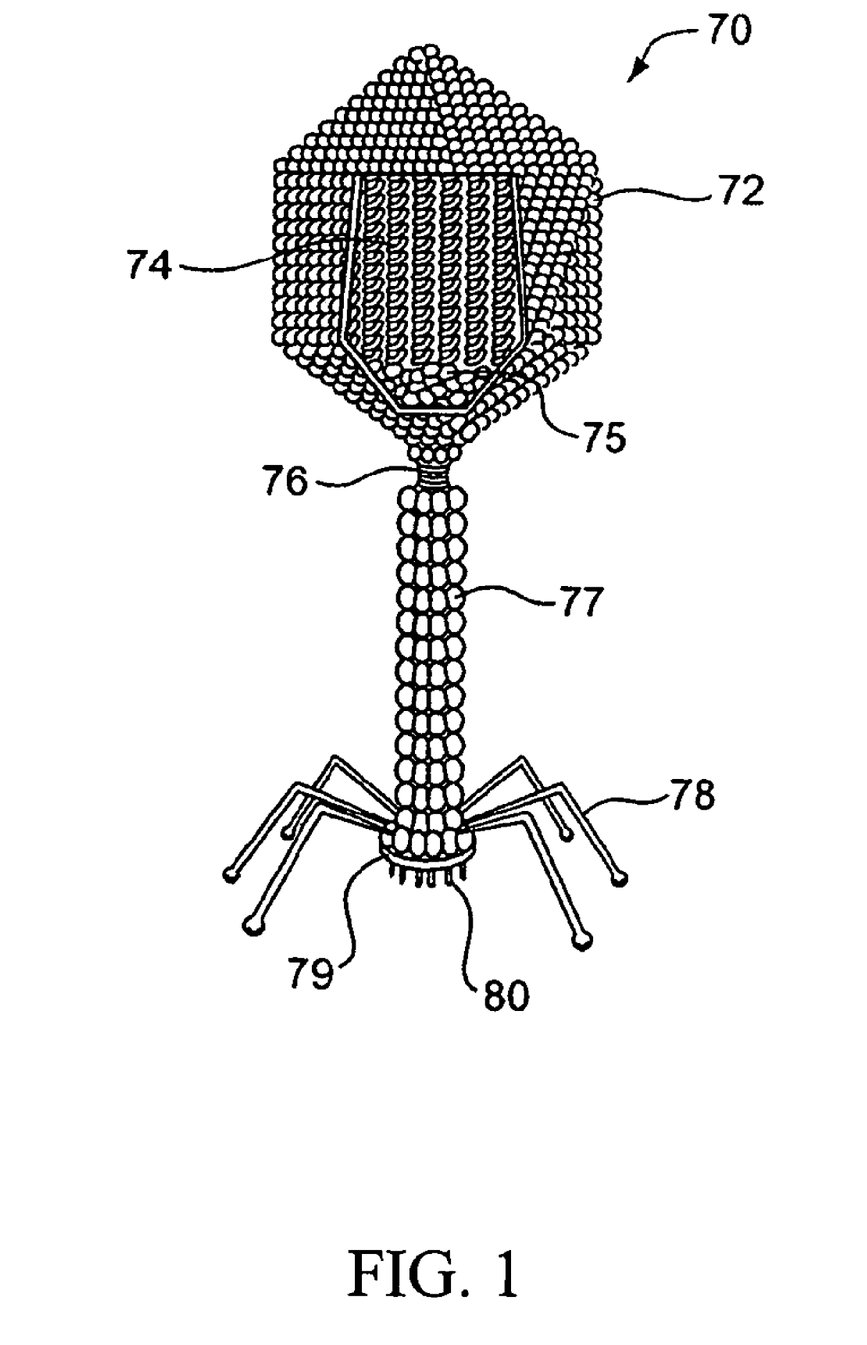
FIG. 1 is an illustration of a bacteriophage.

A typical bacteriophage 70, in this case MS2-*E. Coli* is shown in FIG. 1. Structurally, a bacteriophage 70 comprises a protein shell or capsid 72, sometimes referred to as a head, that encapsulates the viral nucleic acids 74, i.e., the DNA and/or RNA. A bacteriophage may also include internal proteins 75, a neck 76, a tail sheath 77, tail fibers 78, an end plate 79, and pins 80. The capsid 72 is constructed from repeating copies of one or more proteins.

Figure 2:
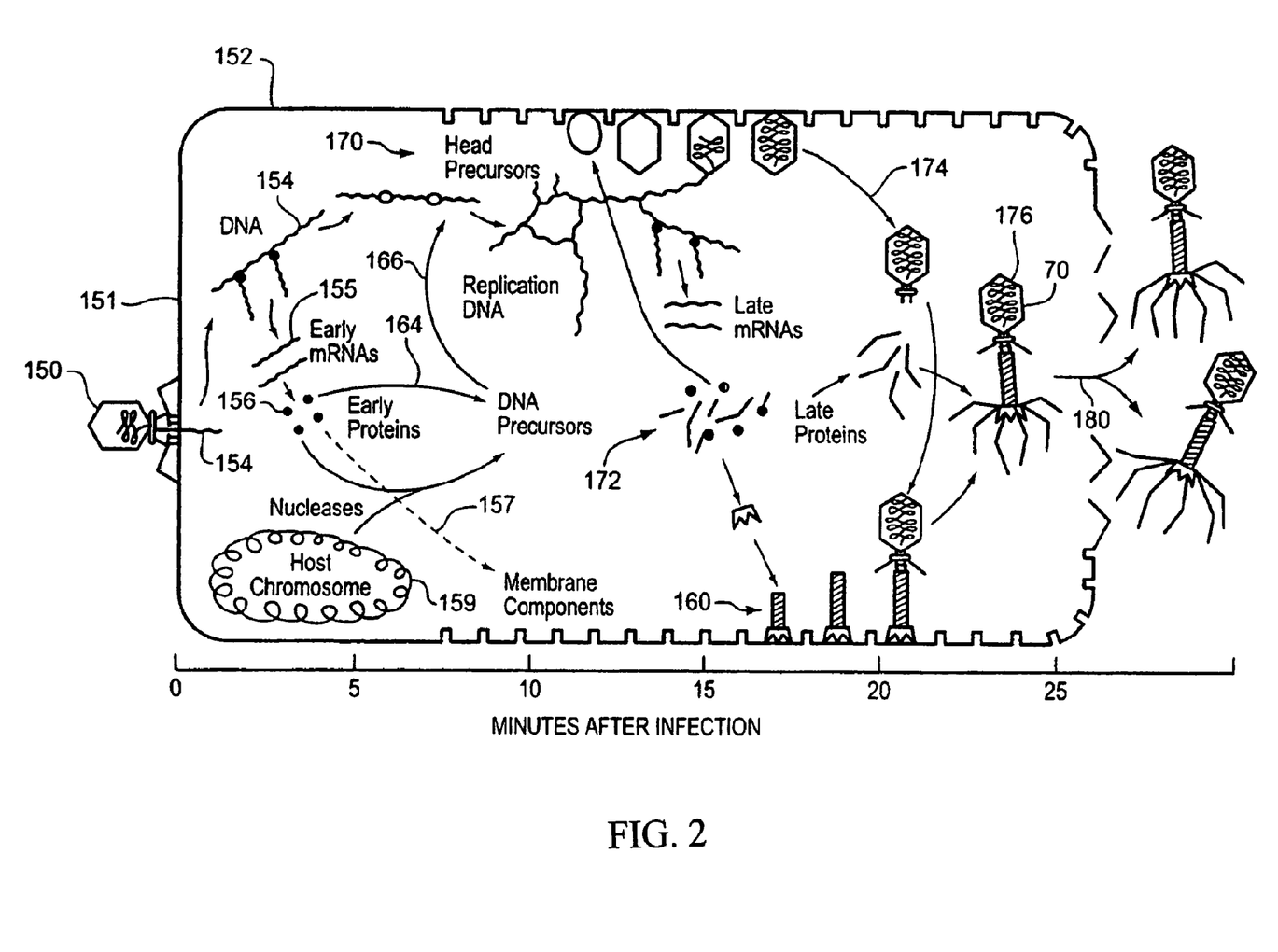
FIG. 2 illustrates a phage amplification process.

Referring to FIG. 2, when a phage 150 infects a bacterium 152, it attaches itself to a particular site on the bacterial wall or membrane 151 and injects its nucleic acid 154 into that bacterium, inducing it to replicate the phage from tens to thousands of copies. The process is shown in schematic in FIG. 2. The DNA evolves to early mRNAS 155 and early proteins 156, some of which become membrane components along line 157 and others of which utilize bacteria nucleases from host chromosomes 159 to become DNA precursors along line 164. Others migrate along the direction 170 to become head precursors that incorporate the DNA along line 166. The membrane components evolve along the path 160 to form the sheath, end plate, and pins. Other proteins evolve along path 172 to form the tail fibers. When formed, the head releases from the membrane 151 and joins the tail sheath along path 174, and then the tail sheath and head join the tail fibers at 176 to form the bacteriophage 70. Some bacteriophage, called lytic bacteriophage, rupture the host bacterium, shown at 180, releasing the progeny phage into the environment to seek out other bacteria.

The total cycle time for phage infection of a bacterium, phage multiplication or amplification in the bacterium, to lysing of the bacterium takes anywhere from minutes to hours, depending on the phage and bacterium in question and the environmental conditions. As an example, the MS2 bacteriophage infects strains of *Escherichia coli* and is able to produce 10,000 copies to 20,000 copies of itself within 40 minutes after attachment to the target cell. The capsid of the MS2 phage comprises 180 copies of an identical protein. This means that for each *E. coli* infected by MS2, upwards of $1.8 \times 10^6$ individual capsid proteins are produced. The process of phage infection whereby a large number of phage and an even larger number of capsid proteins are produced for each infection event is called phage amplification. Note that prior art based bacteriophage detection methods rely upon this amplification process, which as shown in FIG. 2, can take up to several hours to complete.

Microbiologists have isolated and characterized many thousands of phage species, including specific phages for most human bacterial pathogens. Individual bacteriophage species exist that infect bacterial families, individual species, or even specific strains. Table 1 lists illustrative phages and the bacterium they infect.

TABLE 1

| PHAGE | BACTERIAL TARGET |
|---|---|
| MS2 | *E. coli*, *Enterococci* |
| φA11227 | *Yersinia pestis* |
| φFelix 0-1 | *Salmonella* spp. |
| Chp1 | *Chlamydia trachomatis* |
| Gamma | *B. anthracis* |
| A511 | *listeria* spp. |

The present invention can take advantage of the specificity that bacteriophage have toward target bacterium, for example, one can use Gamma phage to specifically interact with *B. anthracis*. Alternatively, some phage species have broad specificity for the bacterial host they infect, and therefore can be used when the type of bacterium present is less important that the mere presence of a bacterium.

Phage Adsorption to Target Microorganism:

In one embodiment, the present invention provides methods, apparatus and compositions for the detection of microorganisms based on the absorption properties of the phage with the target microorganisms. Note that for purposes of the present invention, adsorption refers to the interaction of phage with the surface of target microorganisms. As such, adsorption is used interchangeably with terms like binding, absorption, capture, etc, all of which refer to the interaction between a phage and target microorganisms.

In one aspect of this embodiment, phage are used as surface based signals to indicate the presence of target microorganism, thereby providing a direct indicator of microorganisms within a sample. Embodiments of this aspect of the invention can offer phage-directed specificity for a microorganism, but at a relatively faster speed than existing phage based detection methods, as phage amplification is not required for microorganism detection. As described in greater detail below, detection of target microorganisms using phage binding interactions only requires about two to about ten minutes, and more typically requires only from about two to about six minutes, a significant improvement in time savings over microorganism detection procedures currently in use or on the market.

Embodiments of the present invention utilize the specific interactions between phage and target molecules on the surface of target microorganisms. This phage-microorganism interaction is mediated by specific receptor sites on the surface of the microorganism, e.g., lipopolysaccharides, cell wall proteins, teichoic acid, flagellar proteins, pilus proteins, etc., to which phage specific proteins bind. The interaction between phage and target microorganism is initially reversible and mediated by electrostatic interactions, tending to last several seconds to minutes in duration. However, once the end plate of the phage settles onto the surface of the microorganism, a conformational change takes place in the phage that forces the tail fibers or core through the microorganisms cell wall or membrane, thereby attaching the phage to the surface of the microorganism. This typically occurs within about one to about two minutes of phage-microorganism interaction. Note that phage-microorganism interactions for purposes of the present invention refers to interactions that are maintained under normal microorganism detection assay conditions (however, phage-microorganism interactions may be disrupted by the presence of phage dissociation agents, which are avoided in connection with the present invention). It is the specific nature of this phage-microorganism interaction on the surface of the microorganism that is utilized in the present invention, allowing the phage to act as a detectable label for the presence of the microorganism. The attached phage in this case is accessible to detection as it remains on the surface of the target microorganism for the duration of the detection methods of the invention.

In one embodiment of the present invention phage are flagged with a detectable signal, and preferably a signal that can be viewed with the naked eye. e.g., spectral calorimetric labels such as colloidal gold or colored glass or plastic (e.g. polystyrene, latex, and the like). Preferred flags include colloidal gold nanoparticles (see, for example, Van de Plas and Leunissen, Colloidal Gold as a Marker in Molecular Biology: The Use of Ultra-Small Gold Particles, in "Nonradioactive Labeling and Detection of Biomolecules," C. Kessler, Ed., Springer-Verlag, NY, 1992, pp 116-126, which is incorporated herein by reference). Other flag technologies can be used in accordance with the present invention, for example flagging the phage with fluorescent tags such as fluorescein, rhodamine, and resorufin, and derivatives thereof. In such examples, the fluorescence resonance energy can be measured (see, for example, Cardullo, Nonradioactive Fluorescence Resonance Energy Transfer in "Nonradioactive Labeling and Detection of Biomolecules," C. Kessler, Ed. Springer-Verlag, NY, 1992, pp 414-423, which is incorporated herein by reference) in accordance with the methods of the present embodiments.

Because the present embodiment(s) rely on the exterior binding of phage to microorganism, and not on phage infection and subsequent release of progeny phage (see FIG. 2), the present embodiment(s) can be used in combination with any identified phage species. There is no limitation on phage to be lytic/non-lytic, or for the inclusion of bacterial lysozyme to ensure capture of the target microorganism.

Once a flagged phage is bound to a target microorganism, the protein shell or capsid, neck, tail sheath, end plate, and "flag" remain bound and exposed on the exterior of the microorganism. Typically several hundred to several thousand phage will interact and remain bound to the exterior of each target microorganism thereby providing a significant number of flag signals per microorganism. This exterior phage binding to a target microorganism, in a sense, is comparable to phage amplification reactions that occur within a phage. Of course, as described above, the present invention phage interactions only require a very short amount of time.

Figure 3:
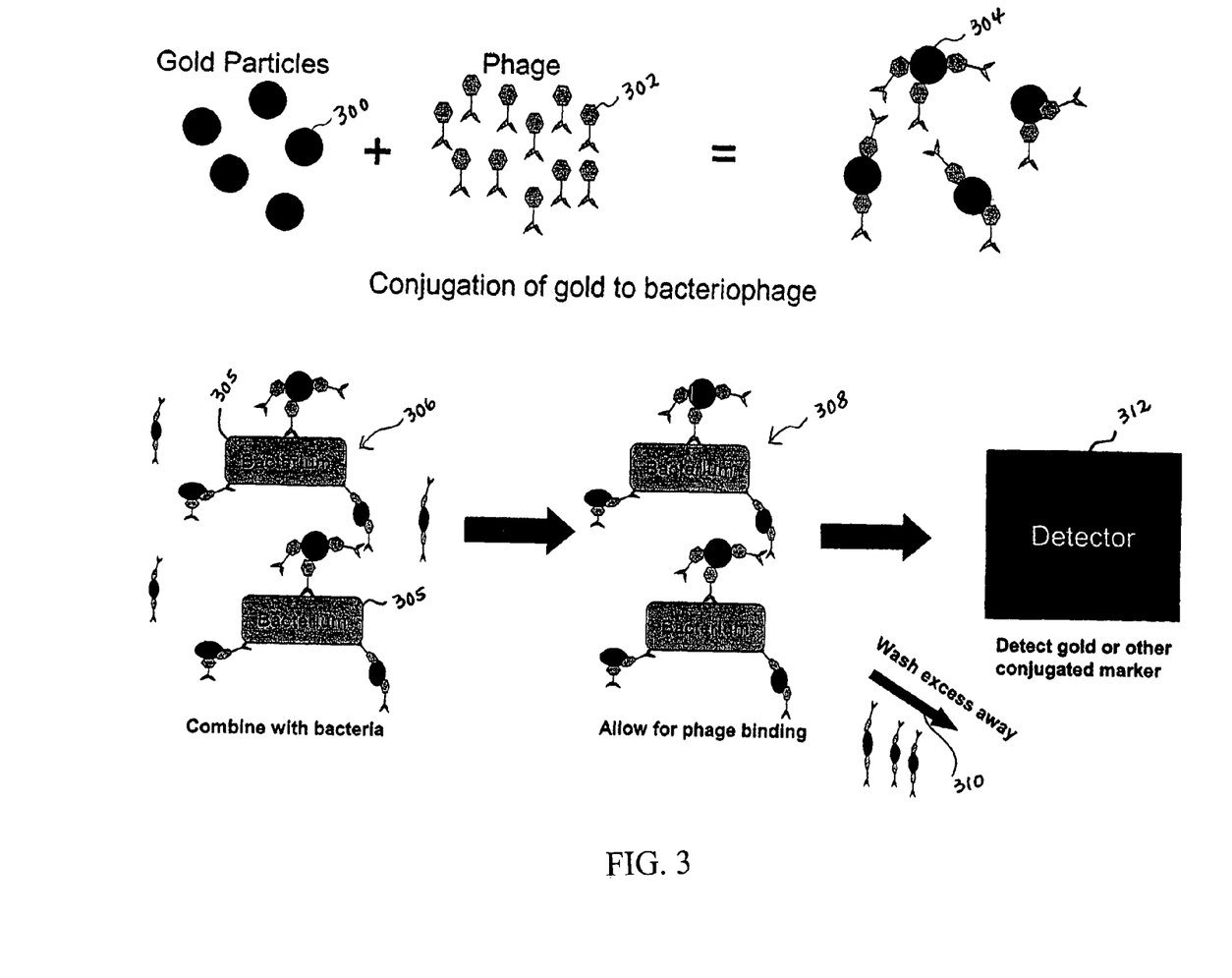
FIG. 3 illustrates another embodiment of the present invention wherein gold conjugated phage are added to a sample for labeling of target bacteria and subsequent detection of the phage labeled microorganism through detection of the gold.

FIG. 3 illustrates one embodiment of the present invention using colloidal gold to label target phage for subsequent microorganism detection. Colloidal gold particles 300 (or other like spectral colorimetric labels, are incubated with a population of target phage 302 to produce colloidal gold labeled phage particles 304. Colloidal gold labeled phage are referred to as flagged phage. Flagged phage are then contacted with a sample being tested for the presence of a microorganism of interest (as shown by reference numeral 306). Interaction (specific and non-specific) between flagged phage and target and non-target microorganisms occur over a period of seconds to several minutes. Specific interactions between flagged phage and target microorganism result in one or more flagged phage (and typically 100s to 1000s) being absorbed to the surface of the microorganism, a bacterium in the present illustration (as shown by reference numeral 308). This interaction occurs within a period of about one to two minutes. The microorganism has now been specifically labeled or flagged using the phage's specificity for the microorganism. Note that aggregates of microorganism and phage may form, thereby enhancing the overall effective concentration of phage flagged microorganisms. Non-bound phage can be removed from the sample via one or more low stringency washes (using a low salt, neutral pH, tris-based buffer, for example) (as shown by arrow 310). Note that various embodiments of the present invention, as discussed more below, show a high ability to differentiate specificity for the phage-microorganism complex from the phage alone, thereby obviating the need for a washing step.

Figure 4:
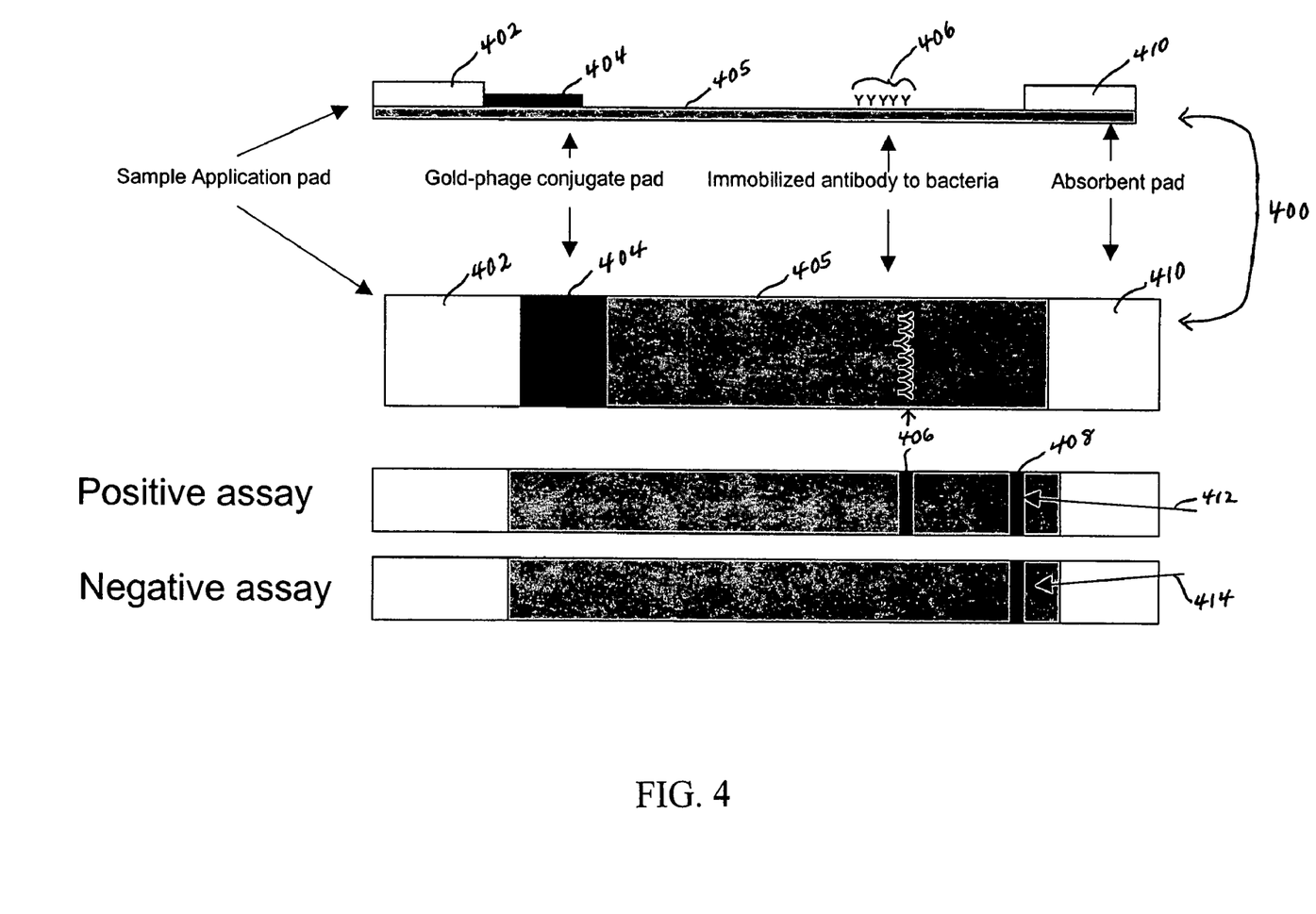
FIG. 4 illustrates one preferred embodiment of the present invention for detection of a microorganism using gold conjugated phage on a lateral flow device; the figure illustrates a side view and top view of a lateral flow device with a conjugate pad consisting of gold conjugated with phage.

Samples can then be analyzed on a detector 312 specific for gold, or on a detector able to concentrate the gold particles for visual recognition (see FIG. 4). Samples can be run concurrently with positive and negative controls to verify the result, i.e., run the reaction in parallel with samples that do not have any bacterium of interest (negative control) or with samples that have a known amount of target bacterium (positive control).

It is also envisioned that standard titers can optionally be prepared, combining known concentrations of target bacteria and known concentrations of flagged phage, for comparison against samples having unknown levels of a target microorganism and known concentrations of flagged phage. As such, the sensitivity of the particular flagged phage interaction with a known amount of a target microorganism can be detected, e.g., 1,000 cells/ml, 10,000 cells/ml, 25,000 cells/ml, and used for comparison sake against an unknown sample, thereby providing information as to the presence and also as to the relative amounts of a microorganism present in the sample. In some instances, this would substitute for the positive control.

Detection assays, as illustrated by FIG. 3, can also be performed to detect multiple bacteria in the same sample, i.e., one species of flagged phage is added to a sample for each target microorganism being tested for, resulting in a single test sample that contains all of the target microorganism and associated phages. Phage flagged microorganism could be segregated using immuno or other like separation techniques and tested for their presence using techniques clear to those skilled in the art and as described above. Alternatively, sample may not be segregated but rather the sample analyzed on one or more detectors specific for each appropriate flag. In this manner, for example, a two to ten minute test could be performed on a blood sample to determine if any one of a target bacterium is present, and an appropriate treatment administered.

Detection of flag phage bound microorganisms is based on the exterior flag. Where the flag is based on colorimetric labels, for example colored beads, the detection is based on specifically immobilizing the target microorganism in a known zone or area. The presence of the flag is then analyzed for within the known zone. For example, the flagged phage is adsorbed to target microorganism, which is then captured by molecules specific for the target microorganism. The combination of flagged phage binding and capture ensures that the target microorganism is present in the sample. Various detection devices can be used in this context, for example lateral flow strip (see FIG. 4), ELISA assays, dot blot assays, and other like procedures. Specific capture molecules for target microorganisms include antibodies, engineered small molecules, ligand-receptor binding pairs, and the like. In one embodiment of an ELISA assay, a microorganism specific antibody is attached to a substrate (for example nitrocellulose). The sample of interest is added to the sample and target microorganism (if present) captured by the immobilized specific antibody. Flagged phage would be added and detected either visually or per the type of flag label. Note that washing steps and positive and negative controls could be used to maximize results. Also note that the flagged phage could be pre-incubated with the sample so that the flagged phage-microorganism (if present) is added to the immobilized antibody. Other combinations could be incorporated into the assay as would be known by one of skill in the art. Another preferred detection device is shown in FIG. 4.

FIG. 4 illustrates a preferred device in accordance with the present embodiment for conveniently detecting the presence or absence of a target microorganism in a sample. A lateral flow device 400, acting as a substrate (or platform) to capture and detect a target microorganism, is shown having a sample application pad 402, a colorimetric-phage conjugation pad 404, a flow zone 405, a microorganism specific immobilization zone 406, one or more control microorganism specific immobilization zones 408 and an absorbent pad 410. Overall the lateral flow device operates under the principle that microorganisms present in a sample interact with flagged phage on the phage conjugation pad in an aqueous environment and begin to diffuse via the flow zone, e.g., a nitrocellulose membrane, away from the sample application pad toward the absorbent pad 410. Immobilized capture molecules, e.g., antibodies, specific for the same target microorganism as the flagged phage capture the flagged microorganism in an immobilization zone 408.

For purposes of the present invention, the term "antibody" is used in the broadest sense and specifically covers monoclonal antibodies, polyclonal antibodies, multispecific antibodies, e.g., bispecific antibodies, chimeric antibodies, humanized antibodies, fully synthetic antibodies and antibody fragments so long as they exhibit the desired biologic activity, i.e., binding specificity.

Concentration of the colorimetric-phage bound microorganism in the zone can be visualized and indicates presence of the microorganism, i.e., a gold line in the case of colloidal gold. Microorganisms and phage not captured in the immobilization zone continue to diffuse until reaching the absorbent pad 410, providing no signal. A positive control flagged phage-microorganism interaction can be run on the same lateral flow device or a separate device (shown as line 412) to indicate the operability of the overall assay. A negative control flagged-phage-non-target microorganism can also be run on the same lateral flow device or a separate device (shown as line 414) to provide a background signal for comparison of the specific signal. Note also that one or more wash steps can be incorporated into the assay to facilitate removal of non-bound flagged-phage and thereby lower the level of non-specific binding or background within each sample run.

Still referring to FIG. 4, sample to be tested is inserted onto the sample application pad 402. Samples generally need to be aqueous in nature, although powdered or solid sample can be administered after dissolution or partial dissolution in an appropriate solvent, e.g., tris-based buffer or the like. Diffusion of the sample from the sample application pad 402 to the immobilization zone 404 typically takes from two to ten minutes, more preferably from two to six minutes and most preferably from about two to five minutes.

In another embodiment involving direct phage signaling, the invention provides a method of detecting the presence or absence of microorganism in a sample to be tested, the method comprising: combing with the sample, parent phage flagged with an appropriate signaling molecule, the parent phage capable of infecting the target microorganism to create a phage exposed sample; providing conditions to the phage exposed sample sufficient to allow the phage to specifically bind to the surface of the target microorganism to create a labeled or detectable microorganism; and assaying the phage labeled microorganism to determine the presence or absence of the microorganism.

The above embodiments are described with reference to a phages' specific interaction(s) with target microorganism surface. Other microorganism labeling agents can be used in replacement of the phage and are within the scope of the present invention. For example, flagged antibodies, e.g., colloidal gold labeled antibodies, specific for epitopes on the surface of target microorganisms can be used to signal the presence of a target microorganism. Other microorganism labeling agents can also be flagged and used in accordance with the present invention, for example target microorganism specific lectins, aptomers, immunoadhesion molecules, and the like. Each flagged-agent serves the same purpose as the flagged-phage, to specifically label the target microorganism.

Finally, it should be noted that a combination of agents can be used to flag label a target microorganism. For example, a non-flagged phage can be used to bind to a target microorganism and a flagged-agent, for example an flagged-antibody, specific for the bound phage, can be incubated with the sample to thereby indirectly label the target microorganism. Other flagging combinations can be envisioned, wherein the object of the combination is to specifically label the target microorganism with a detectable signal.

The present invention also provides kits for detecting microorganisms in a sample. Kits of the invention typically include a flagged phage specific for a target microorganism, a substrate having one or more capture molecules immobilized thereon (specific for the target microorganism), various reagents and buffers useful in capture of the flagged microorganism on the substrate, and directions for use and understanding of the detector. Note that more than one type of flagged phage can be included in a kit, as can more than one substrate having an immobilization zone for capture of target microorganisms. In one embodiment of the kit the substrate is a lateral flow device. In some embodiments the substrate and capture molecule are separate, requiring the capture molecule to be applied to the substrate.

Having generally described the invention, the same will be more readily understood by reference to the following examples, which are provided by way of illustration and are not intended as limiting.

Lateral Flow Device Example:

In the following example, the MS2 phage is used to detect $E.\ coli$ in the process of FIG. 1. Lateral flow strips, as illustrated in FIGS. 3 and 4, were prepared with polyclonal antibodies that specifically bind to the MS2 phage.

Determining the MS2 Detection Limit of the Lateral Flow Strips—Bacteriophage MS2 (ATCC 15597-B1) was prepared from infected $E.\ coli$ (ATCC 15597) cells on a confluent plate. The concentration of viable MS2 from this preparation was $2 \times 10^7$ pfu/mL by plaque assay. A dilution series of this MS2 stock was made to produce a range of from $1 \times 10^7$ pfu/mL to $1 \times 10^5$ pfu/mL. MS2 was detected with the lateral flow strips. Results are shown in Table 2.

TABLE 2

| MS2 Dilution | MS2 Concentration (pfu/mL) | Lateral Flow Result (line intensity) |
|---|---|---|
| 1/2 | $1 \times 10^7$ | + |
| 1/20 | $1 \times 10^6$ | +/− |
| 1/200 | $1 \times 10^5$ | − |

Line intensity was determined visually 15 minutes after loading a sample into a lateral flow strip. Line intensity was ranked on a scale ranging from "++" indicating maximum line intensity to "−" indicating no detectable line. "+/−" indicates a line that is barely detectable. The results of this assay indicate that the detection limit of MS2 on the lateral flow strips prepared for these tests is 1.times.10.sup.6 pfu/mL.

Determining *E. coli* Detection Limits and Total Testing Times—*E. coli* (ATCC 15597) from a saturated culture were diluted to produce raw samples having concentrations of $1\times10^8$, $1\times10^7$, $1\times10^6$, $1\times10^5$, $1\times10^4$, $1\times10^3$, and $1\times10^2$ cells/mL. MS2 was added to each raw sample to give test samples with MS2 concentrations of $1\times10^6$ pfu/mL. The test samples were incubated for 1 hour to 5 hours at 37° C. After incubation, the test samples were diluted 10:1 such that the parent MS2 concentration was $1\times10^5$ pfu/mL—below the established detection limit. The test samples were then analyzed using the lateral flow strips. The results are shown in Table 3.

TABLE 3

| *E. Coli* Concentration (cells/mL) | *E. coli* in Reaction (cells) | Lateral Flow Result (line intensity) | | | |
|---|---|---|---|---|---|
| | | 1 hour | 2 hours | 3 hours | 4 hours |
| $1 \times 10^7$ | $1 \times 10^6$ | + | ++ | ++ | ++ |
| $1 \times 10^6$ | $1 \times 10^5$ | + | ++ | ++ | ++ |
| $1 \times 10^5$ | $1 \times 10^4$ | − | + | ++ | ++ |
| $1 \times 10^4$ | $1 \times 10^3$ | − | − | + | ++ |
| $1 \times 10^3$ | $1 \times 10^2$ | − | − | − | + |

These results show that 100 *E. coli* cells can be detected after 4 hours using the disclosed invention. Higher levels of *E. coli* ($1\times10^5$ cells or more) are detectable after 1 hour.

Similarly, the lateral flow strip process described above has also been used successfully to detect the *salmonella choleraesuis* bacteria using the PRD-1 bacteriophage, the *bacillus anthracis* bacteria using the gamma phage, and the group B *Streptococcus* using the B-30 bacteriophage.

There has been described a microorganism detection method which is specific to a selected organism, sensitive, simple, fast, and/or economical, and having numerous novel features. The invention can be used in a wide variety of applications including human clinical diagnostics, veterinary diagnostics, food pathogen detection, environmental testing, and biowarfare detection. It should be understood that the particular embodiments shown in the drawings and described within this specification are for purposes of example and should not be construed to limit the invention, which will be described in the claims below. Further, it is evident that those skilled in the art may now make numerous uses and modifications of the specific embodiment described, without departing from the inventive concepts. Equivalent structures and processes may be substituted for the various structures and processes described; the subprocesses of the inventive method may, in some instances, be performed in a different order; or a variety of different materials and elements may be used. Consequently, the invention is to be construed as embracing each and every novel feature and novel combination of features present in and/or possessed by microorganism detection apparatus and methods described.

This specification contains numerous citations to publications and patents. Each is hereby incorporated by reference for all purposes.

The invention claimed is:

1. A method of determining the presence of a target microorganism in a sample, the method comprising:
   combining with the sample an amount of flagged phage capable of binding to an outside surface of the target microorganism to create a flag labeled target microorganism;
   providing conditions and an amount of time sufficient to allow the flagged phage to bind to the outside surface of the target microorganism; and
   assaying the phage exposed sample to detect the presence of the flag labeled microorganism, without detecting phage amplified within the target microorganism and, wherein presence of the flag bound to the outside surface of the target microorganism indicates presence of the microorganism,
   wherein the detecting the presence of the flag labeled microorganism is by concentrating the flag labeled microorganism to enhance the capacity to detect the flag labeled microorganisms, and
   wherein the concentrating of flag labeled microorganisms is on a flow strip device having one or more immobilization zones, wherein the flag labeled microorganisms are captured and concentrated within the one or more immobilization zones.

2. The method of claim 1 wherein the flagged phage is a phage labeled with colorimetric particles.

3. The method of claim 2 wherein the colorimetric particles are colloidal gold particles.

4. The method of claim 1 wherein the flagged phage is a phage labeled with a fluorescent tag.

* * * * *